United States Patent
Eng et al.

(10) Patent No.: US 7,785,155 B2
(45) Date of Patent: Aug. 31, 2010

(54) RETRACTABLE CONTACT POST SHIELD AND METHOD

(75) Inventors: Edmond C. Eng, Kirkland, WA (US); Michael Anthony Schoch, Granite Falls, WA (US); B. Matthew Marzynski, Seattle, WA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 12/359,093

(22) Filed: Jan. 23, 2009

(65) Prior Publication Data

US 2009/0126990 A1 May 21, 2009

Related U.S. Application Data

(62) Division of application No. 11/853,713, filed on Sep. 11, 2007, now Pat. No. 7,481,683.

(51) Int. Cl.
*H01R 4/48* (2006.01)
(52) U.S. Cl. ..................................................... 439/729
(58) Field of Classification Search ................ 439/145, 439/725, 729, 775, 786, 816–819
See application file for complete search history.

(56) References Cited

U.S. PATENT DOCUMENTS

| | | | | |
|---|---|---|---|---|
| 1,808,545 A | 6/1931 | Grace | ......................... | 439/263 |
| 5,421,749 A | 6/1995 | Schrauder | .................... | 439/786 |
| 5,457,392 A | 10/1995 | Filipescu | ..................... | 324/555 |
| 5,814,996 A | 9/1998 | Winter | ........................ | 324/510 |
| 6,231,361 B1 | 5/2001 | Ko et al. | ...................... | 439/172 |
| 7,081,026 B2 | 7/2006 | Schwarz | ..................... | 439/729 |

FOREIGN PATENT DOCUMENTS

| | | |
|---|---|---|
| DE | 30 46 957 A1 | 7/1982 |
| DE | 36 10 009 A1 | 10/1987 |
| EP | 0045834 | 5/1981 |
| EP | 0 045 834 A1 | 2/1982 |
| EP | 0707358 | 4/1996 |
| GB | 2059181 | 4/1981 |
| GB | 2256978 | 12/1992 |
| WO | 2005/013435 | 2/2005 |

*Primary Examiner*—Khiem Nguyen
(74) *Attorney, Agent, or Firm*—Dorsey & Whitney LLP

(57) ABSTRACT

An electronic device having one or more contact posts is disclosed having a sleeve slidably mounted around the contact post and lockable by a push-push latching system in a retracted position in which the sleeve is below an upper end of the contact post and an extended position in which the sleeve extends around and covers the upper end of the contact post. The sleeve and contact post may have respective apertures extending transversely therethrough, which are aligned when the sleeve is slightly retracted to receive a probe. Alternatively, an ECG electrode clip may engage an end of the contact post when it is exposed by the sleeve being in the retracted position.

11 Claims, 7 Drawing Sheets

RETRACTABLE CONTACT POST SHIELD AND METHOD

CROSS-REFERENCE TO RELATED APPLICATION

This application is a divisional application of U.S. patent application Ser. No. 11/853,713, filed Sep. 11, 2007. The entire disclosure of the prior application, from which a copy of the oath or declaration is supplied, is considered to be part of the disclosure of the instant application and is hereby incorporated by reference therein.

TECHNICAL FIELD

This invention relates to electrical testing equipment, and, more particularly to an apparatus and method for preventing accidental electric shock in testing equipment having exposed contact posts.

BACKGROUND OF THE INVENTION

Medical equipment must be carefully tested and calibrated in order to ensure that it will function properly in critical situations. Electrocardiogram (ECG) testers are an example of such test equipment. As shown in FIG. 1, an ECG tester 10 typically includes a number of contact posts 12 that may be coupled to electrode leads of an ECG monitor by means of clips 14. The ECG tester 10 must be able to test ECG monitors having a wide variety of electrode lead clips. Some of these lead clips normally clip to electrodes having exposed terminals. Therefore, the contact posts 12, like the electrode terminals, must be exposed rather than insulated from external contact by an insulating structure.

Hospital equipment, including ECG monitors, must be tested to ensure that they do not pose a shock hazard resulting from short circuits to an AC line power lead. The ECG leads, as well as cases of ECG monitors, are normally isolated from AC line voltage by suitable insulation, which can become damaged. ECG testers check electrical isolation of ECG monitors by applying line voltage to the contact posts 12. The exposed contact posts 12 in prior art systems can be hazardous inasmuch as they can be inadvertently touched and cause electrocution. Accordingly, it would be an advancement in the art to provide a conveniently used apparatus and method for shielding the contact posts of ECG testers and like equipment when they are not covered by an electrode clip.

SUMMARY OF THE INVENTION

In one aspect of the invention, an electronic device, such as an ECG tester, includes a contact post having first and second ends mounted on a housing having the first end exposed and the second end electrically coupled to a circuit board operable to apply signals to and receive signals from the contact post. An insulative sleeve is slidably mounted on the contact post and engages a latching mechanism that secures the sleeve in either of two positions, an extended position in which the sleeve is positioned over the contact post in order to protect and insulate the post and a retracted position in which the first end of the contact post is exposed.

In another aspect of the invention the latching mechanism is a push-push latch. An engagement member may be secured to the sleeve to enable a user to push the sleeve into the retracted and extended positions.

In another aspect of the invention, the sleeve has an aperture extending transversely through a wall thereof such that a clip, such as a banana plug, may engage the first end of the contact post when the sleeve is in the extended position.

DETAILED DESCRIPTION OF PREFERRED EMBODIMENTS

Figure 1:
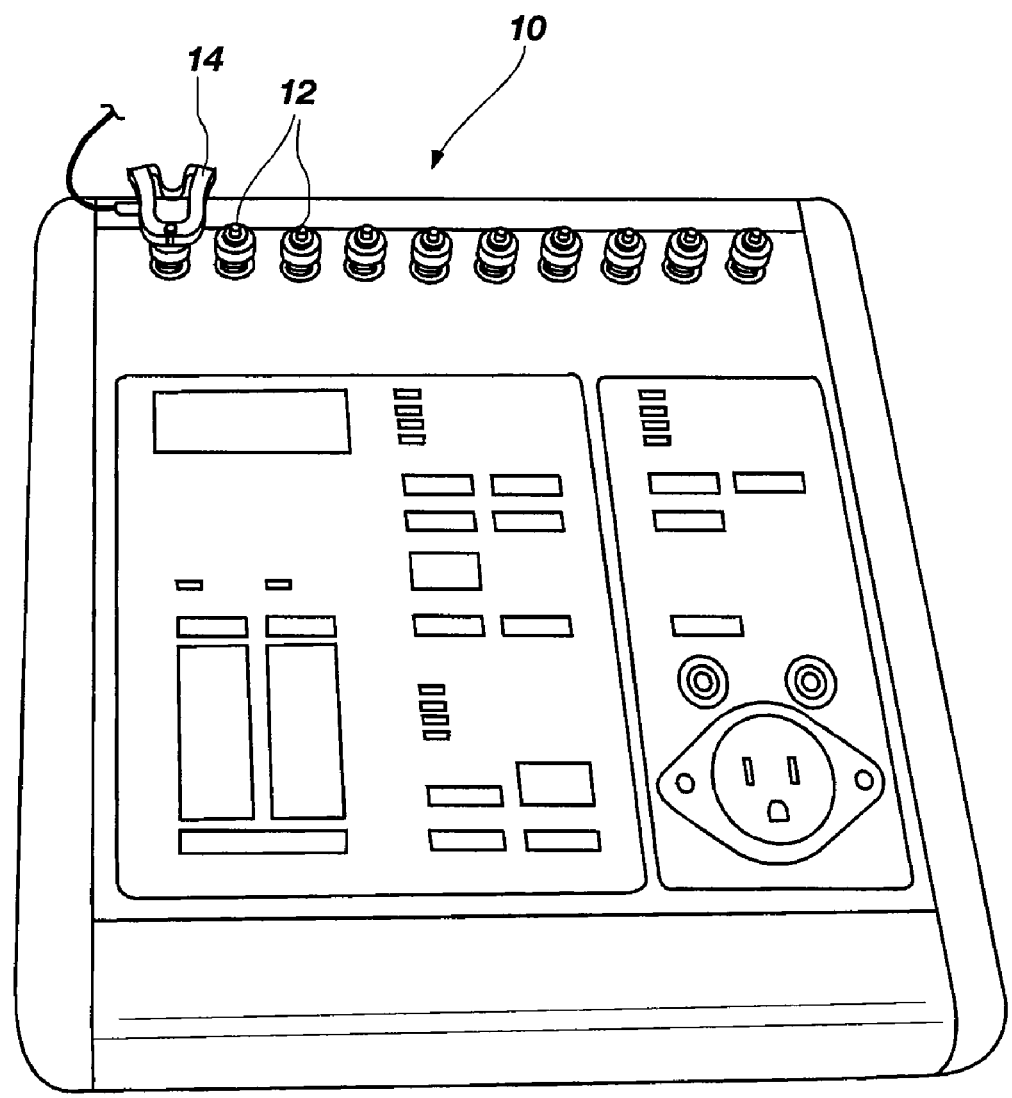
FIG. 1 is an isometric view of an ECG tester in accordance with the prior art.
Figure 2A:
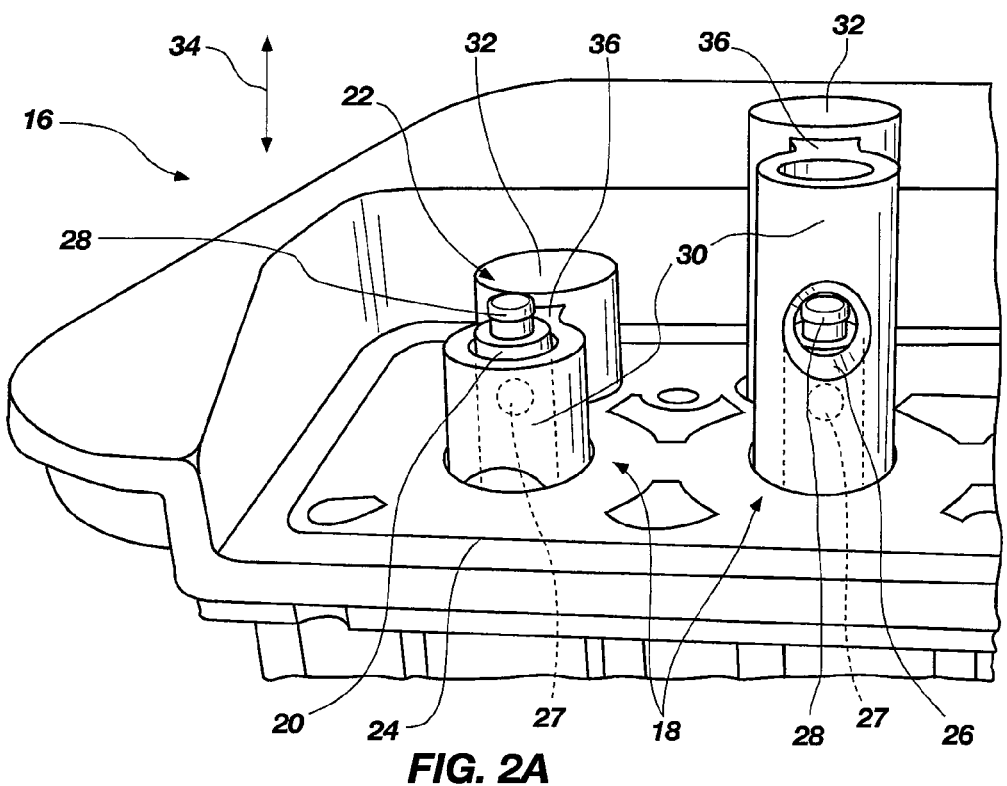
FIGS. 2A-2B are isometric views of an ECG tester having contact post shields in accordance with an embodiment of the invention.
Figure 2B:
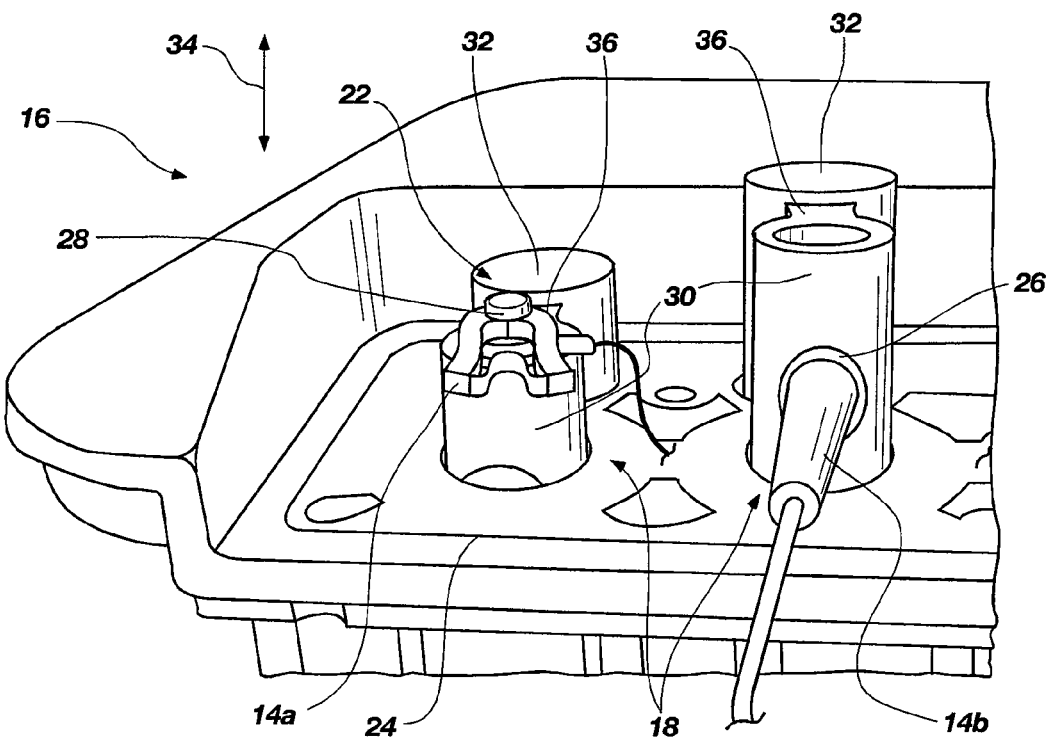

Referring to FIGS. 2A and 2B, in one embodiment of the invention, an ECG tester 16 includes a plurality of insulating shields 18 positioned around respective contact posts 20. The shields 18 are in the form of cylindrical sleeves 30 that are slidably positioned around respective contact posts 20, but other configurations can be used. The shields 18 are positionable in a retracted position leaving an upper end 22 of the contact post 20 extending from the shield 18 and an extended position in which the upper end 22 is positioned within the shield 18. The upper end 22 of the contact post 20 is shaped to be engaged by conventional ECG electrode clips. In some embodiments, in the extended position, the shield 18 extends beyond the top of the contact post 20 a substantial distance, such as a distance about equal or greater than the extent the top of the shield 18 is below the top of the contact post 20 in the retracted position. The shield 18 may be coupled to the housing 24 by means of a push-push latching system such that an operator may push a retracted shield 18 to cause it to spring back to the extended position and push an extended shield 18 to lock it in the retracted position.

In some embodiments, the shield 18 includes an aperture 26 that extends through a wall of the shield 18. When the shield 18 is retracted slightly, but not enough to expose the upper end 22 of the contact post 20, the aperture 26 is aligned with an aperture 27 formed in the contact post 20. As shown in FIG. 2B, when the shield 18 is retracted slightly further from the position shown in FIG. 2A, a banana plug 14b may be inserted through the aperture 26 in the shield 18 and the aperture 27 in the contact post 20. The contact post 20 may include a narrowed upper portion 28 sized to receive a connector, such as an ECG clip 14a when the shield 18 is in the fully retracted position.

An engagement member 32 may be secured to the sleeve 30 and provide an area for a user to safely press to move the sleeve 30 into the extended and retracted positions of FIGS. 2A and 2B. In the illustrated embodiment, the engagement member 32 has a cross section that is constant for a portion of its length along a direction of movement 34 of the shield 18 as it moves between the retracted and extended positions. For example, the engagement member 32 is substantially cylindrical in the illustrated embodiment, however many other cross sectional shapes may be used such as rectangular, hexagonal, I- or H-shaped, or some other shape having a keyway, or any polygon offering sufficient structural shape. The engagement member 32 may be secured to the sleeve 30 by a web 36 of material, which may serve to increase the separation between the engagement member 32 and the contact post 20 to reduce the risk of accidental electrical shocks to an operator.

Figure 3:
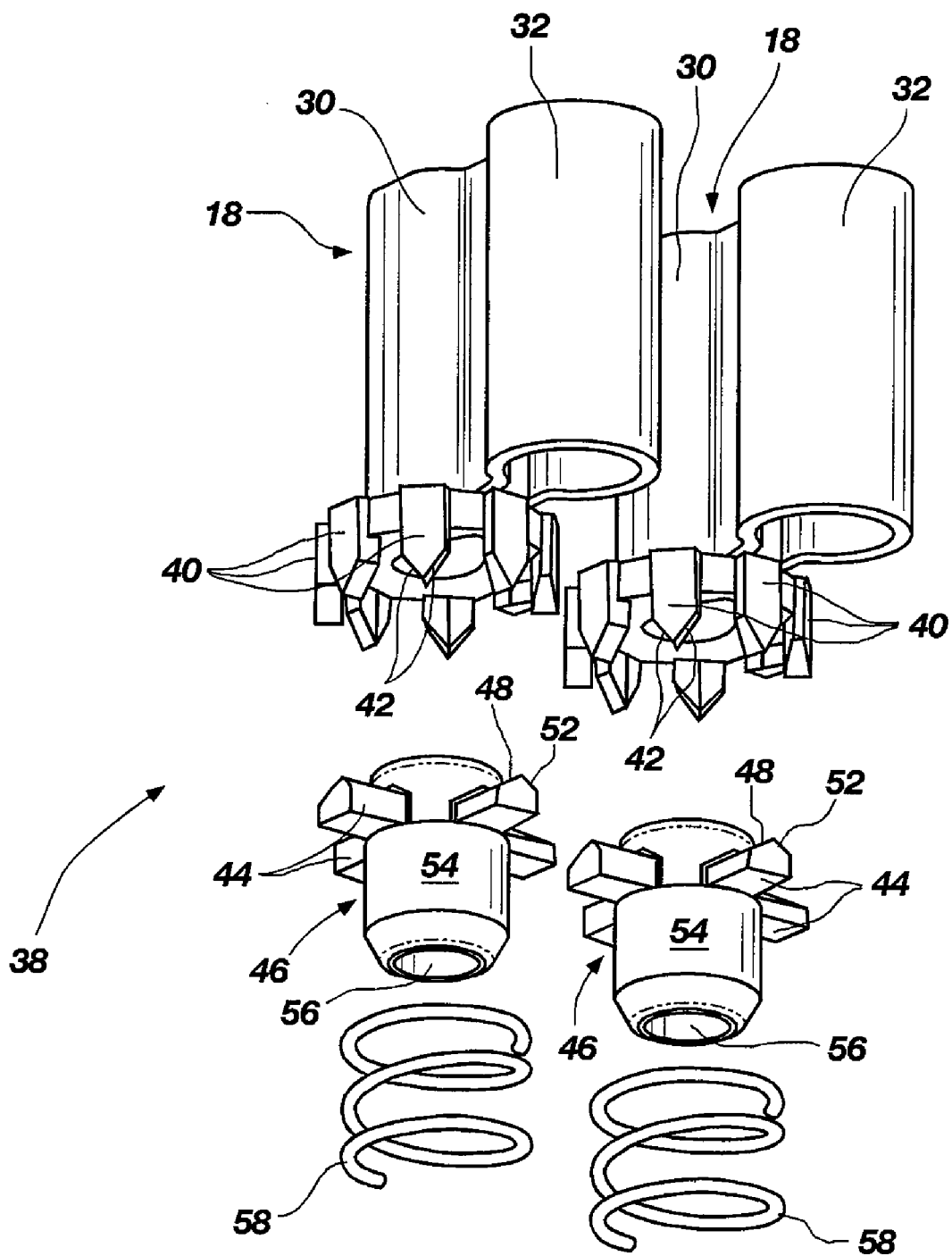
FIG. 3 is an exploded view of a contact post shield in accordance with an embodiment of the present invention.
Figure 4:
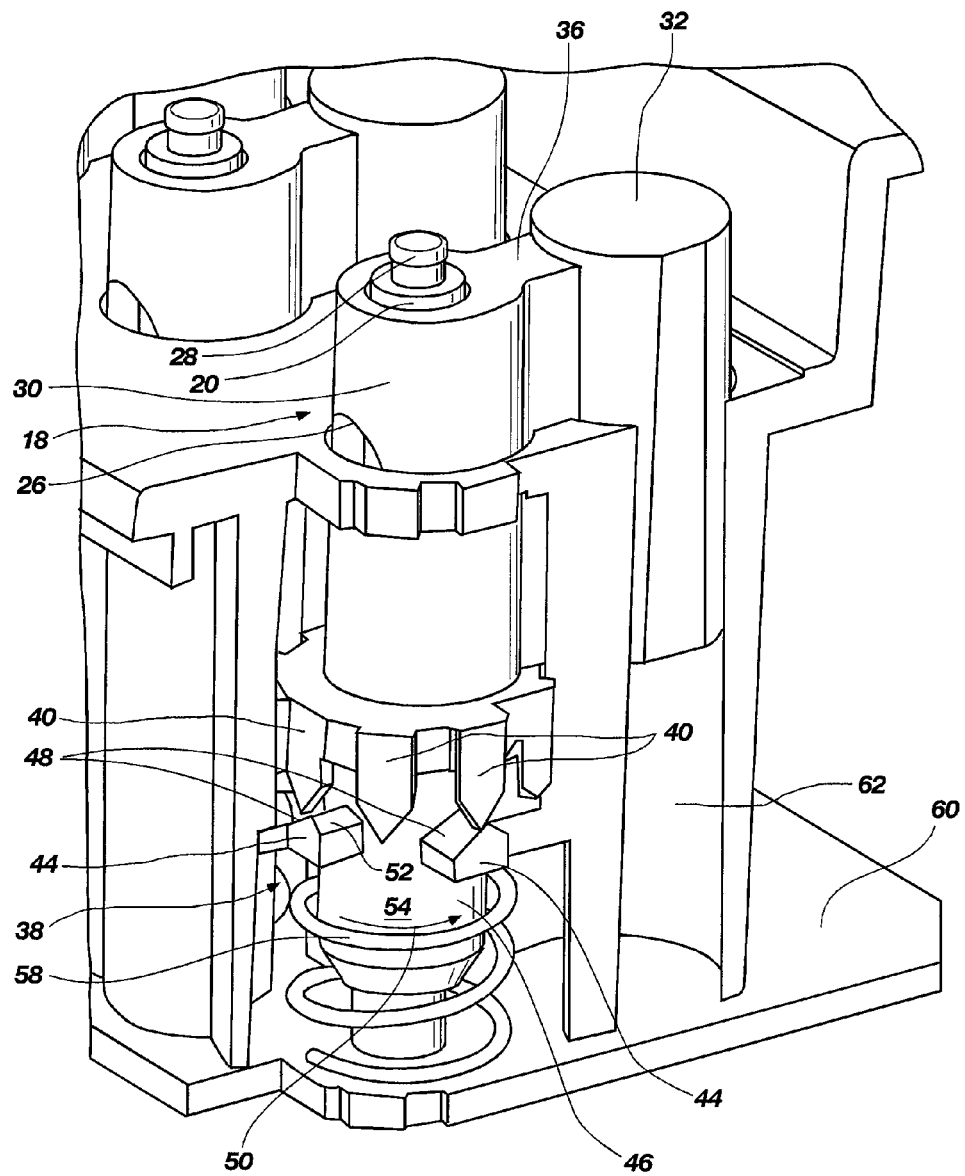
FIG. 4 is a cutaway isometric view of a contact post shield mounted within an ECG tester in accordance with an embodiment of the present invention.

Referring to FIGS. 3 and 4, a latching mechanism 38, such as a push-push latching mechanism, secures the shield 18 in either the extended or retracted position. The latching mechanism may be any push-push type latching mechanism or other latching mechanism known in the art. In the illustrated embodiment, the latching mechanism 38 includes indexing members 40 secured to the sleeve 30. The indexing members 40 may include pointed ends formed by intersecting sloped surfaces 42. The indexing members 40 are distributed evenly around the sleeve 30 and may be positioned slightly radially outwardly from the sleeve 30 with a gap between each adjacent members 40.

The indexing members 40 engage arms 44 formed on a ratchet 46. The arms 44 include sloped surfaces 48, such that pressing the indexing members 40 against the arms 44 causes the ratchet to rotate in direction 50 (FIG. 4). In the illustrated embodiment, there are twice as many indexing members 40 as arms 44, that is, eight indexing members 40 and four arms 44. The arms 44 may bear another sloped surface 52 sloping in the opposite direction from the sloped surface 48 such that the sloped surfaces 48, 52 form a point. The surface 52 is preferably substantially narrower than the surface 48, however they may also be of equal width. The arms 44 secure to a ratchet hub 54 having an aperture 56 for receiving the contact post 20. A biasing member 58, such as a spring or other resilient member, engages the ratchet hub 54 and urges the sloped surfaces 48 against the indexing members 40. In the illustrated embodiment, the biasing member 58 extends between the arms 44 of the ratchet hub 54 and a printed circuit board 60 (FIG. 4) to which the contact post 20 is mounted. The circuit board 60 may be an ECG tester control circuit for applying line voltages to the contact posts 20 and receiving signals from the contact posts 20. The engagement member 32 may slide within a channel 62. Slidable engagement of the engagement member 32 within the channel 62 may advantageously fix the rotational position of the indexing members 40 relative to the ratchet 46.

Figure 5:
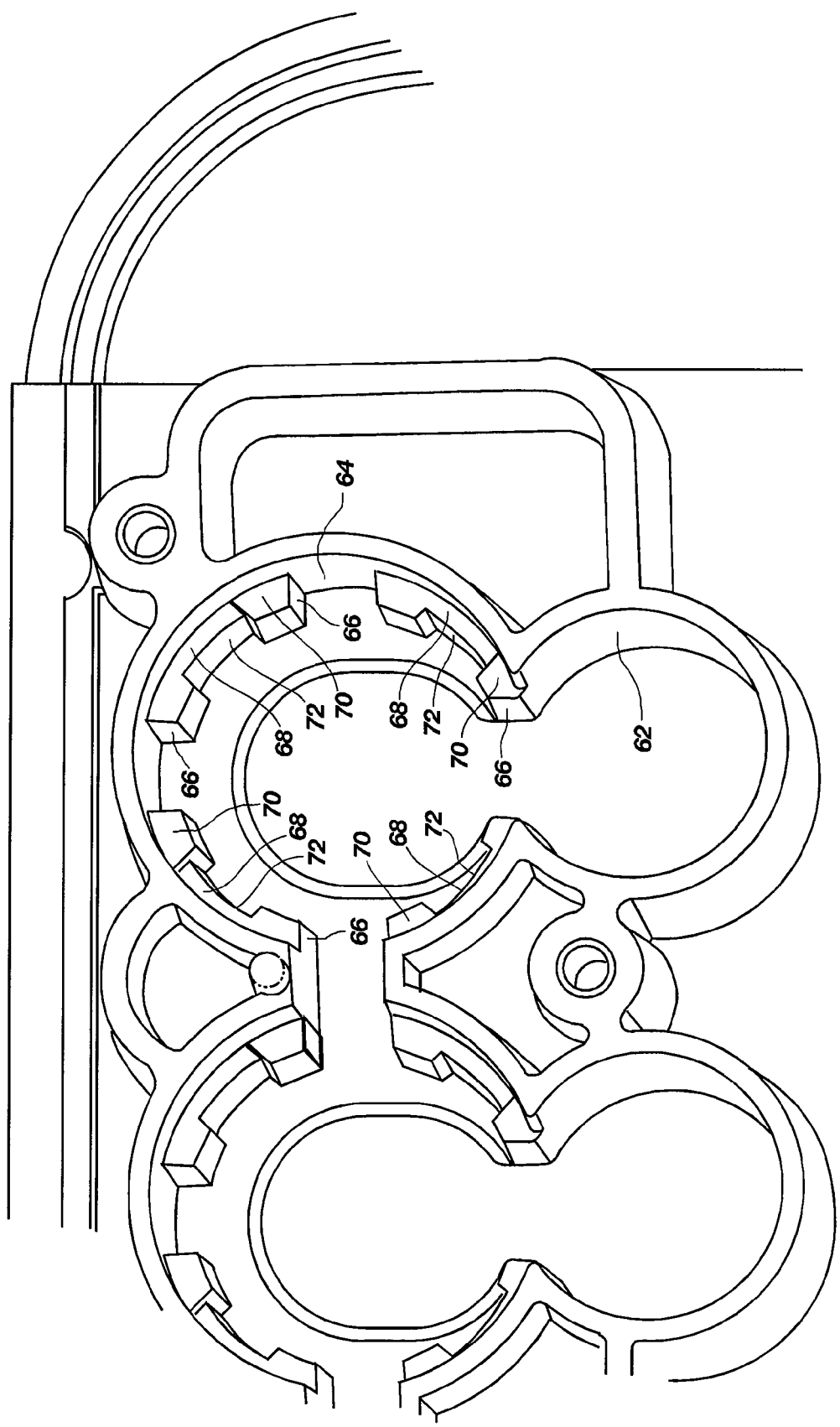
FIG. 5 is an isometric view of a housing suitable for mounting a contact post shield in accordance with an embodiment of the present invention.

Referring to FIG. 5, the sleeve 30 and ratchet 46 may mount within a channel 64 having vertical guides 66 formed therein. The vertical guides 66 may be equal in number to the arms 44 of the ratchet 46 and sized to slidably receive the arms 44. The vertical guides 66 constrain the ratchet to movement in the vertical direction when the arms 44 are positioned therein. Stops 68 are positioned between the vertical guides 66 and likewise may be equal in number to the arms 44 of the ratchet 46. The stops 68 prevent upward movement of the arms 44 when the arms 44 are aligned therewith. The stops 68 may have a sloped surface such that when the arms 44 are urged against the stops 68, they are urged against a raised area 70 that prevents further rotation until the arms 44 are pushed away from the stops 68. Grooves 72 may be formed in the stops 68 to receive the indexing members 40. In the illustrated embodiments, the vertical guides 66 are formed by gaps between the stops 68.

Figure 6A:
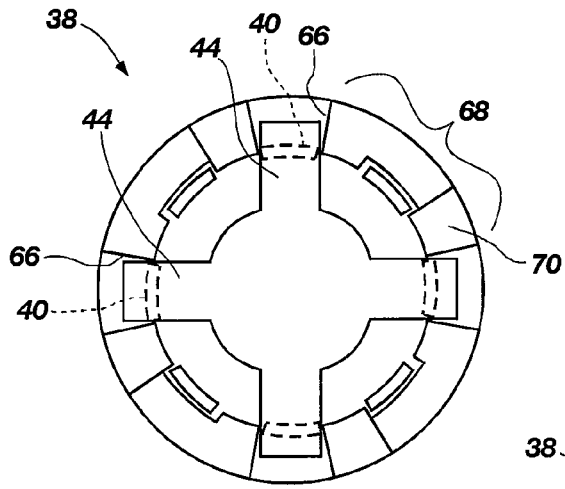
FIGS. 6A-6C are bottom plan views of a latching mechanism in accordance with an embodiment of the present invention.
Figure 6B:
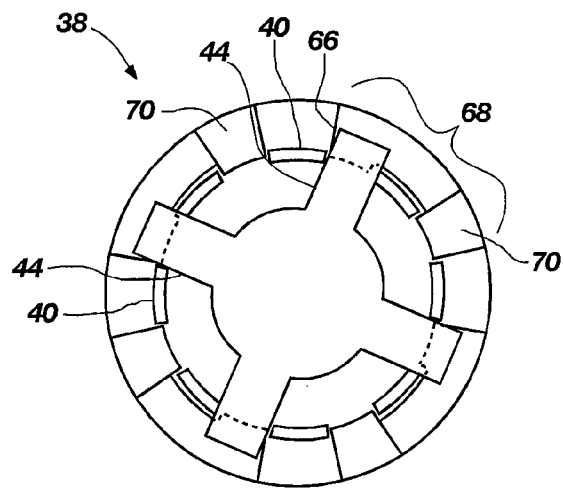
Figure 6C:
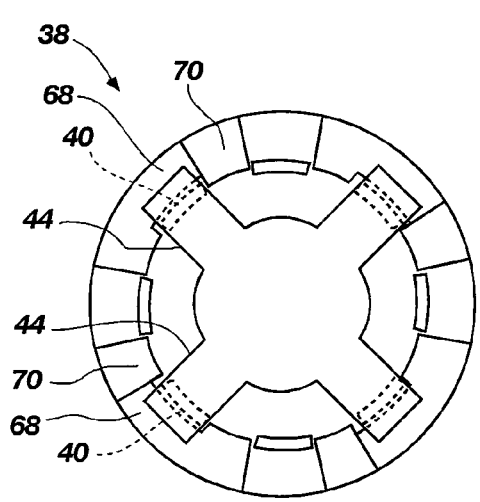

Referring to FIGS. 6A-6C, while referring generally to FIGS. 4 and 5, the function of the illustrated latching mechanism 38 will be more particularly pointed out. When the shield 18 is in the extended position, the arms 44 are positioned within the vertical guides 66, as shown in FIG. 6A, such that the biasing member 58 is able to urge the shield 18 upwardly. To move the shield 18 into the retracted position, the operator pushes downwardly on the engagement member 32, which causes the indexing members 40 to press against the sloped upper surface 48 of the ratchet 46, causing the arms 44 rotate over the edges of vertical guide 66, as shown in FIG. 6B. Upon release of the engagement member 32, the biasing member 58 urges the sloped upper surface 48 against the sloped surface of stop 68, causing the ratchet and arms 44 to rotate and move into alignment with another of the indexing members 40, stopping against the raised portion of 70, as shown in FIG. 6C. As is apparent in FIG. 6C, the arms 44 are positioned over the stops 68 such that they are constrained from moving upwardly. To move from the retracted position to the extended position, the operator pushes downwardly on the engagement member 32, the indexing members 40 are again urged against the sloped upper surfaces 48, causing the arms 44 to rotate over the raised portion of 70 and into alignment with the vertical guides 66, as shown in FIG. 6A, where they are allowed to move vertically upward upon release of the engagement member 32.

Figure 7:
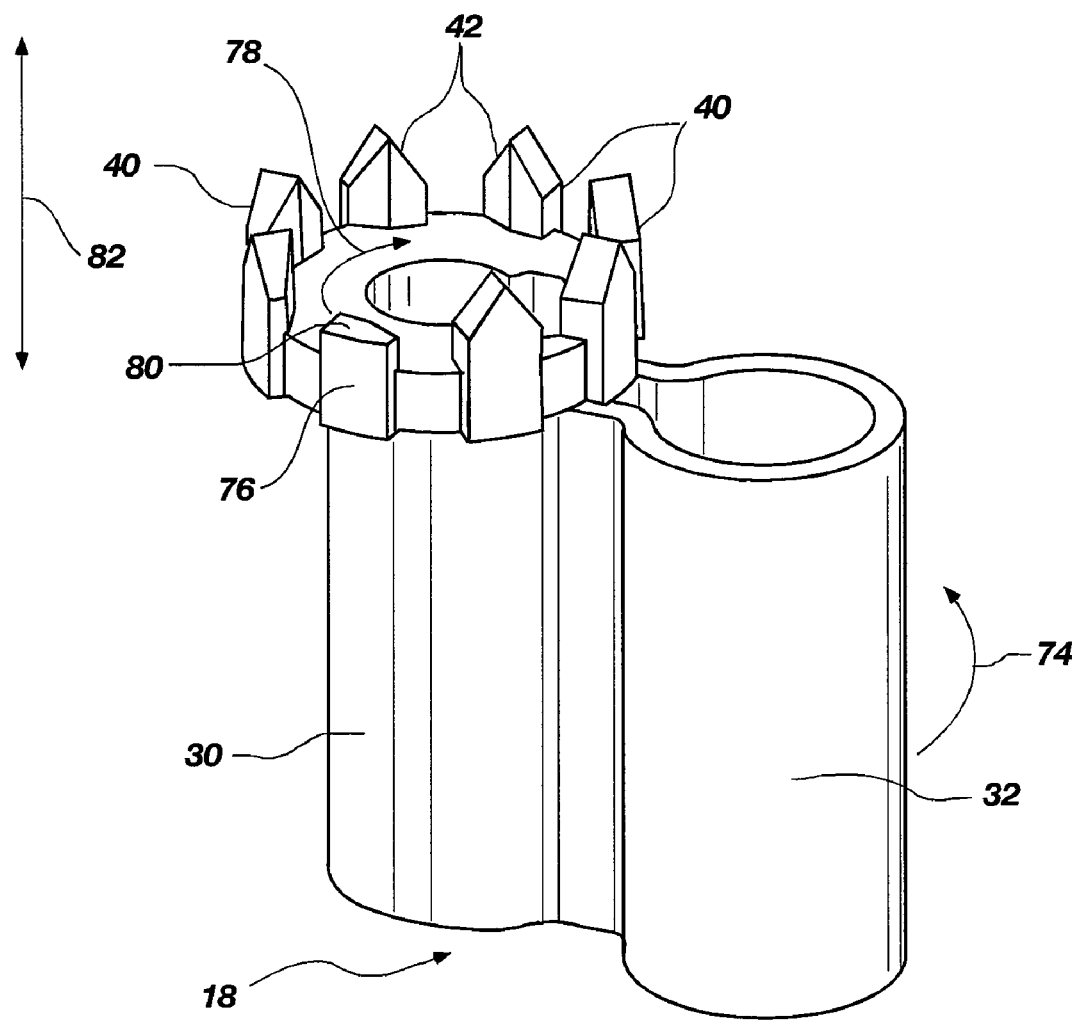
FIG. 7 is bottom isometric view of an alternative embodiment of a shield having a truncated indexing member in accordance with an embodiment of the present invention.

Referring to FIG. 7, in embodiments where the engagement member 32 is secured to the shield 18, pressing on the engagement member may result in a rotational moment 74 being exerted on the shield 18 inasmuch as the engagement member 32 is offset from the shield 18. As a result, the indexing members 40 may tend to become misaligned from the sloped upper surfaces 48. In particular, indexing member 76 that is located about 90 degrees from the engagement member moving along the direction of rotation 78 may tend to move over the surface 52 such that it will exert a force on the surface 52 opposite the direction of rotation 78 of the ratchet 46. Accordingly, the indexing member 76 may be truncated such that it does not have sloped surfaces 42. The indexing member 76 may have instead a flat upper surface 80 that is offset from the pointed ends of the other indexing members 40 along the direction 82 of movement of the sleeve 18 such that the flat upper surface 80 does not contact the sloped surfaces 48, 52 of the ratchet 46. In the illustrated embodiment, a portion of the indexing member 76 remains and aids in registering the shield 18 within a vertical guide 66 or groove 72. In an alternative embodiment, there is no indexing member located in the position of indexing member 76. In yet another alternative embodiment, the sloped surfaces 42 of the indexing member 76 may be of different lengths such that the point formed by the surfaces 42 is shifted opposite the direction of rotation 78 in order to compensate for shifting caused by the rotational moment 74.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the invention is not limited except as by the appended claims.

What is claimed is:

1. A method for preventing accidental electric shock comprising:

moving an insulating sleeve from an extended position in which the sleeve extends around and covers a contact post to a retracted position in which an end of the contact post is exposed;

latching the insulating sleeve in the retracted position;

attaching an electrode lead to the exposed end of the contact post while the insulating sleeve is in the retracted position;

subsequently removing the electrode lead from the contact post; and after removing the electrode lead from the contact post, returning the sleeve to its extended position.

2. The method of claim 1 wherein the sleeve includes a transverse aperture formed in a wall thereof, the contact post includes a transverse aperture extending therethrough, and the method further comprises:

moving the sleeve toward the retracted position so that the aperture of the sleeve is aligned with the aperture of the contact post; and inserting a probe through the aligned apertures.

3. The method of claim 1 wherein the sleeve further includes an engagement member secured to the sleeve and extending outwardly therefrom, and wherein the act of moving the sleeve from an extended position in which the sleeve extends around and covers a contact post to a retracted position from the extended position to the retracted position comprises moving the sleeve by pressing the engagement member.

4. The method of claim 1, further comprising resiliently biasing the sleeve to its extended position so that the act of moving the insulating sleeve from the extended position to the retracted position comprises exerting a force on the sleeve against the resilient bias.

5. The method of claim 1, further comprising unlatching the sleeve to allow the resilient bias to move the sleeve from the retracted to the extended position.

6. The method of claim 5, wherein the act of unlatching the sleeve comprises:

pushing downwardly on the sleeve against the resilient bias to urge a plurality of discrete urging members secured to the sleeve circumferentially spaced apart from one another such that at least one of the discrete urging members presses against at least one sloped upper surface secured to a ratchet slidably mounted relative to the housing thereby causing the ratchet to slide downwardly against a biasing member and out of engagement with at least one vertical guide constraining rotation of the ratchet, the ratchet rotating in a first direction upon coming out of engagement with the vertical guides under the force of the at least one of the urging members on the sloped upper surface; and releasing the discrete urging members such that the resilient bias urges the ratchet upwardly against a stop positioned adjacent the vertical guide.

7. The method of claim 6, wherein:

the sleeve further includes an engagement member secured to the sleeve and extending outwardly therefrom; and the act of moving the sleeve from an extended position in which the sleeve extends around and covers a contact post to a retracted position from the extended position to the retracted position comprises moving the sleeve by pressing the engagement member;

the at least one sloped upper surface includes a plurality of sloped upper surfaces;

the sleeve moves between the extended and protracted positions along a longitudinal axis; and wherein the discrete urging members are disposed such that none of the discrete urging members engage the sloped upper surface of the plurality of sloped upper surfaces having a portion thereof located angularly about 90 degrees in the first direction about the longitudinal axis from an angular position of the engagement member.

8. The method of claim 6, further comprising:

again downwardly urging the plurality of discrete urging members such that at least one of the discrete urging members presses against the at least one sloped upper surface such that the ratchet rotates out of engagement with the stop and into engagement with a second vertical guide adjacent the stop; and again releasing the discrete urging members such that the biasing member urges the ratchet upwardly within the vertical guide thereby urging the discrete urging members and sleeve to move upwardly.

9. A method for preventing accidental electric shock comprising:

moving an insulating sleeve comprising a transverse aperture formed in a wall thereof from an extended position in which the sleeve extends around and covers a contact post to a retracted position in which the transverse aperture of the insulative sleeve is aligned with a transverse aperture extending through the contact post;

inserting a probe through the aligned apertures of the sleeve and the contact post;

subsequently removing the probe from the contact post; and after removing the probe from the contact post, returning the sleeve to its extended position.

10. The method of claim 9 wherein the sleeve further includes an engagement member secured to the sleeve and extending outwardly therefrom, and wherein the act of moving the sleeve from an extended position in which the sleeve extends around and covers a contact post to a retracted position from the extended position to the retracted position comprises moving the sleeve by pressing the engagement member.

11. The method of claim 9, further comprising resiliently biasing the sleeve to its extended position so that the act of moving the insulating sleeve from the extended position to the retracted position comprises exerting a force on the sleeve against the resilient bias.

* * * * *